(12) United States Patent
Stonger et al.

(10) Patent No.: US 10,016,549 B2
(45) Date of Patent: Jul. 10, 2018

(54) ALERT ON A DIALYSIS MACHINE

(71) Applicant: Fresenius Medical Care Holdings, Inc., Waltham, MA (US)

(72) Inventors: Christine Vivian Stonger, Tustin, CA (US); Palmer David Updyke, Walnut Creek, CA (US); John Arrizza, San Diego, CA (US); Michelle Bayly, Abington, MA (US); Phil Swenson, Placentia, CA (US); DaVeeda Callie Mason, Irvine, CA (US); Edward Royal, Mission Viejo, CA (US); Gaudencio D. Barredo, Jr., South San Francisco, CA (US); Sandra S. Gadeyne, Escondido, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 0 days.

(21) Appl. No.: 14/723,735

(22) Filed: May 28, 2015

(65) Prior Publication Data
US 2016/0346451 A1    Dec. 1, 2016

(51) Int. Cl.
*A61M 1/14*        (2006.01)
*B01D 61/24*       (2006.01)
(Continued)

(52) U.S. Cl.
CPC ............. *A61M 1/14* (2013.01); *B01D 61/243* (2013.01); *A61M 1/1601* (2014.02);
(Continued)

(58) Field of Classification Search
CPC ..................................................... A61M 1/14
See application file for complete search history.

(56) References Cited

U.S. PATENT DOCUMENTS

| 8,117,699 B2 | 2/2012 | Richards et al. |
| 8,180,654 B2 | 5/2012 | Berkman et al. |

(Continued)

FOREIGN PATENT DOCUMENTS

| CN | 203631132 U | 6/2014 | |
| JP | 2010-009437 A | * 1/2010 | ............... G06F 3/06 |

(Continued)

OTHER PUBLICATIONS

U.S. Appl. No. 14/670,777, filed Mar. 27, 2015, 29 pages.
(Continued)

*Primary Examiner* — Peter Keyworth
(74) *Attorney, Agent, or Firm* — Fish & Richardson P.C.

(57) ABSTRACT

A dialysis machine comprising: a first sensor for detecting motion of a patient; a second sensor for detecting a health condition of the patient; a processing module for: controlling dialysis functions of a dialysis treatment; receiving information related to a status of the dialysis treatment in which toxins are removed from blood of the patient; receiving, from the first sensor, information related to the motion of the patient; receiving, from the second sensor, information related to the health condition of the patient; and identifying an emergency condition based at least in part on the information related to the motion of the patient, the information related to the health condition of the patient, and the information related to the status of the dialysis treatment; and a transceiver for: in response to identifying an emergency condition, sending a notification that includes patient information to one or more remote entities.

27 Claims, 5 Drawing Sheets

(51) Int. Cl.
*A61M 1/16* (2006.01)
*A61M 1/36* (2006.01)

(52) U.S. Cl.
CPC ....... *A61M 1/3656* (2014.02); *A61M 2205/18* (2013.01); *A61M 2205/3553* (2013.01); *A61M 2205/3569* (2013.01); *A61M 2205/3576* (2013.01); *A61M 2205/3584* (2013.01); *A61M 2205/3592* (2013.01); *A61M 2205/52* (2013.01); *A61M 2230/04* (2013.01); *A61M 2230/30* (2013.01)

(56) References Cited

U.S. PATENT DOCUMENTS

| | | |
|---|---|---|
| 8,608,658 B2 | 12/2013 | Burbank et al. |
| 2004/0100376 A1 | 5/2004 | Lye et al. |
| 2005/0065445 A1 | 3/2005 | Arzbaecher et al. |
| 2005/0131332 A1* | 6/2005 | Kelly ................. A61M 1/1696 604/4.01 |
| 2006/0015368 A1 | 1/2006 | Hockey |
| 2006/0135907 A1 | 6/2006 | Remde et al. |
| 2007/0016452 A1 | 1/2007 | Wilson et al. |
| 2008/0212746 A1 | 9/2008 | Gupta et al. |
| 2010/0317955 A1* | 12/2010 | Madsen ............... A61B 5/0478 600/377 |
| 2011/0082445 A1* | 4/2011 | Van der Helm .. A61M 5/14244 604/890.1 |
| 2012/0088466 A1 | 4/2012 | Conroy |
| 2012/0138533 A1 | 6/2012 | Curtis et al. |
| 2013/0018301 A1 | 1/2013 | Weaver et al. |
| 2013/0109965 A1* | 5/2013 | Assman ................ A61M 5/484 600/431 |
| 2015/0025449 A1 | 1/2015 | Yuds et al. |

FOREIGN PATENT DOCUMENTS

| | | |
|---|---|---|
| JP | 2010009347 A | 1/2010 |
| JP | 2012095717 A | 5/2012 |
| WO | WO2008027967 A1 | 3/2008 |
| WO | WO2010006147 A1 | 1/2010 |

OTHER PUBLICATIONS

Notification of Transmittal of the International Search Report and the Written Opinion of the International Searching Authority from the corresponding PCT Application No. PCT/US2016/027452, dated Sep. 28, 2016, 20 pages.

* cited by examiner

ALERT ON A DIALYSIS MACHINE

TECHNICAL FIELD

This disclosure relates to alerts on a dialysis machine.

BACKGROUND

Dialysis is a treatment used to support a patient with insufficient renal function. Dialysis machines are typically equipped with alert functionality. For example, some dialysis machines activate alarms when certain conditions occur. When an alarm is activated, the dialysis machine may take an action. For example, the dialysis machine may produce an audio alert to notify a patient or a medical care professional that the alarm has been activated.

SUMMARY

In one aspect, a dialysis machine includes a first sensor for detecting motion of a patient. The dialysis machine also includes a second sensor for detecting a health condition of the patient. The dialysis machine also includes a processing module for controlling dialysis functions of a dialysis treatment. The processing module is also for receiving information related to a status of the dialysis treatment in which toxins are removed from blood of the patient. The processing module is also for receiving, from the first sensor, information related to the motion of the patient. The processing module is also for receiving, from the second sensor, information related to the health condition of the patient. The processing module is also for identifying an emergency condition based at least in part on the information related to the motion of the patient, the information related to the health condition of the patient, and the information related to the status of the dialysis treatment. The dialysis machine also includes a transceiver for, in response to identifying an emergency condition, sending a notification that includes patient information to one or more remote entities.

Implementations can include one or more of the following features.

In some implementations, the dialysis machine also includes a dialysate cassette configured to be fluidly connected to one or more dialysate containers by one or more dialysate container lines. The dialysis machine also includes a dialysate pump for pumping dialysate from one or more of the dialysate containers, through the dialysate cassette, through a patient line, to an abdomen of the patient. The dialysate pump is also for drawing spent dialysate from the abdomen of the patient, through a drain line, through the dialysate cassette, to a drain. The spent dialysate includes toxins that are removed from the blood of the patient.

In some implementations, the dialysis machine also includes a dialysate pump for pumping dialysate through a first portion of a dialyzer. The dialysis machine also includes a blood pump for drawing blood from the patient through a second portion of the dialyzer. The dialyzer is configured to remove toxins from the blood of the patient and collect the toxins in the dialysate.

In some implementations, the second sensor is a blood pressure sensor and the information related to the health condition of the patient is blood pressure information.

In some implementations, the second sensor is a heart rate sensor and the information related to the health condition of the patient is heart rate information.

In some implementations, the second sensor is a moisture sensor.

In some implementations, the moisture sensor is for detecting whether a needle has been dislodged from the patient.

In some implementations, the dialysis machine also includes an alert mechanism for generating an alert directed at the patient indicating that a potential emergency condition has been identified. The alert mechanism is also for receiving, from a patient, input indicating that the potential emergency condition is not an emergency condition.

In some implementations, the alert mechanism is a device that is in wireless communication with the dialysis machine. The device includes a button that, when pressed by the patient, indicates that the potential emergency condition is not an emergency condition.

In some implementations, the device is configured to wirelessly receive patient information from the dialysis machine.

In some implementations, the dialysis machine also includes a button that, when engaged, causes the notification that includes the patient information to be sent to the one or more remote entities.

In some implementations, the button is located on a device that is in wireless communication with the dialysis machine.

In some implementations, the device is a bracelet.

In some implementations, the patient information includes location information related to the patient.

In some implementations, the location information related to the patient includes a geographic location of the dialysis machine.

In some implementations, the patient information includes one or more of a medical condition of the patient, demographic information of the patient, a preferred hospital of the patient, a medication list of the patient, allergies of the patient, information related to the patient's treatment, emergency contact associated with the patient, and medical personnel associated with the patient.

In some implementations, the remote entities include one or more of 911 EMS, a nurse, a doctor, and an emergency contact of the patient.

In another aspect, a dialysis machine includes a processing module for controlling dialysis functions of a dialysis treatment. The processing module is also for receiving information related to a status of the dialysis treatment in which toxins are removed from blood of a patient. The processing module is also for receiving information related to a health condition of the patient. The dialysis machine also includes a data communications interface. The data communications interface includes a port on the dialysis machine that interfaces with a portable memory device that includes an alert mechanism. The data communications interface also includes an interface control system for managing download of patient information to the portable memory device. The patient information is based at least in part on the status of the dialysis treatment and the information related to the health condition of the patient.

Implementations can include one or more of the following features.

In some implementations, the portable memory device is a universal serial bus (USB) memory device, the data communications interface is a USB data communications interface, the port on the dialysis machine is a USB port, and the interface control system is a USB interface control system.

In some implementations, the dialysis machine also includes a dialysate cassette configured to be fluidly connected to one or more dialysate containers by one or more dialysate container lines. The dialysis machine also includes a dialysate pump for pumping dialysate from one or more of the dialysate containers, through the dialysate cassette, through a patient line, to an abdomen of the patient. The dialysate pump is also for drawing spent dialysate from the abdomen of the patient, through a drain line, through the dialysate cassette, to a drain. The spent dialysate includes toxins that are removed from the blood of the patient.

In some implementations, the dialysis machine also includes a dialysate pump for pumping dialysate through a first portion of a dialyzer. The dialysis machine also includes a blood pump for drawing blood from the patient through a second portion of the dialyzer. The dialyzer is configured to remove toxins from the blood of the patient and collect the toxins in the dialysate.

In some implementations, the dialysis machine also includes a button that, when engaged, causes patient information to be downloaded to the portable memory device. The button, when engaged, also causes a notification to be sent to one or more remote entities that includes some or all of the patient information.

In some implementations, the button is a physical button positioned on a housing of the dialysis machine.

In some implementations, the button is a virtual button on a touch screen of the dialysis machine.

In some implementations, the alert mechanism is configured to generate an alert directed at an emergency responder. The alert is for informing the emergency responder that the portable memory device contains patient information that is relevant to a patient's emergency condition.

In some implementations, the alert is an audio tone.

In some implementations, the alert is a flashing light.

In some implementations, the patient information includes one or more of a medical condition of the patient, demographic information of the patient, a preferred hospital of the patient, a medication list of the patient, allergies of the patient, information related to the patient's treatment, and medical personnel associated with the patient.

In another aspect, a portable memory device is configured to receive patient information from a dialysis machine. The portable memory device includes an alert mechanism configured to generate an alert directed at an emergency responder. The alert is for informing the emergency responder that the portable memory device contains patient information that is relevant to a patient's emergency condition.

Implementations can include one or more of the following features.

In some implementations, the portable memory device is a universal serial bus (USB) memory device.

In some implementations, the alert is an audio tone.

In some implementations, the alert is a flashing light.

In some implementations, the patient information includes one or more of a medical condition of the patient, demographic information of the patient, a preferred hospital of the patient, a medication list of the patient, allergies of the patient, information related to the patient's treatment, emergency contact associated with the patient, and medical personnel associated with the patient.

Implementations can include one or more of the following advantages.

In some implementations, the dialysis machine includes an emergency notification feature for sending an emergency notification to a remote entity. A patient who is receiving dialysis treatment can press a button on the dialysis machine to cause the emergency notification to be sent. The notification can include information related to the patient's location to assist the remote entity in finding the patient. The notification can also include information related to the patient's medical condition, thereby preparing the remote entity to deal with the particular emergency condition.

In some implementations, the dialysis machine may generate an intermediate alert indicating that a potential emergency condition has been identified. The dialysis machine can refrain from sending the notification if the dialysis machine receives a notification that the potential emergency condition is not, in fact, an emergency condition. In some implementations, the dialysis machine is configured to receive input from the patient that indicates whether or not the potential emergency condition is an emergency condition.

In some implementations, patient information is stored on an alert mechanism or a USB memory device that is configured to communicate with the dialysis machine. The patient may need to be transported to a medical facility to receive treatment in response to the emergency condition. By having patient information stored on the alert mechanism or the USB memory device, information that may be helpful for administering treatment to the patient can accompany the patient wherever he or she is situated.

Other aspects, features, and advantages of the invention will be apparent from the description and drawings, and from the claims.

DETAILED DESCRIPTION

Dialysis machines typically use alert systems for notifying patients and operators of various operating conditions. Certain dialysis machines described herein include an emergency notification feature for sending an emergency notification to a remote entity, such as 911 EMS, in the case of an emergency. The dialysis machines can, for example, include a button that, when pressed, causes the emergency notification to be sent.

In an example, the emergency notification is sent if a dialysis machine detects a series of conditions that indicate that the patient may be in danger. The dialysis machine can include a motion sensor that is configured to detect patient movements. If the motion sensor does not detect patient movement for a specified period of time, a primary condition is satisfied which indicates that a potentially dangerous condition may exist.

Once the dialysis machine determines that a potentially dangerous condition may exist, the dialysis machine can determine whether one or more secondary conditions are satisfied. Secondary conditions can be related to conditions of the patient that are measured by biometric sensors. For example, the dialysis machine can include a blood pressure cuff for detecting the patient's blood pressure, and if the patient's blood pressure is above or below a particular threshold, a secondary condition can be satisfied. As a result, the dialysis machine determines that the patient may be in danger, and an emergency notification is sent to the remote entity.

Alternatively, once the dialysis machine determines that a potentially dangerous condition may exist, the dialysis machine may be configured to generate a notification directed to the patient. The notification can be an alarm (e.g., an audible or visual alarm) intended to get the patient's attention. If the patient does not respond to the notification, the dialysis machine may determine that the patient could be in danger, and an emergency notification may be sent to the remote entity.

Figure 1:
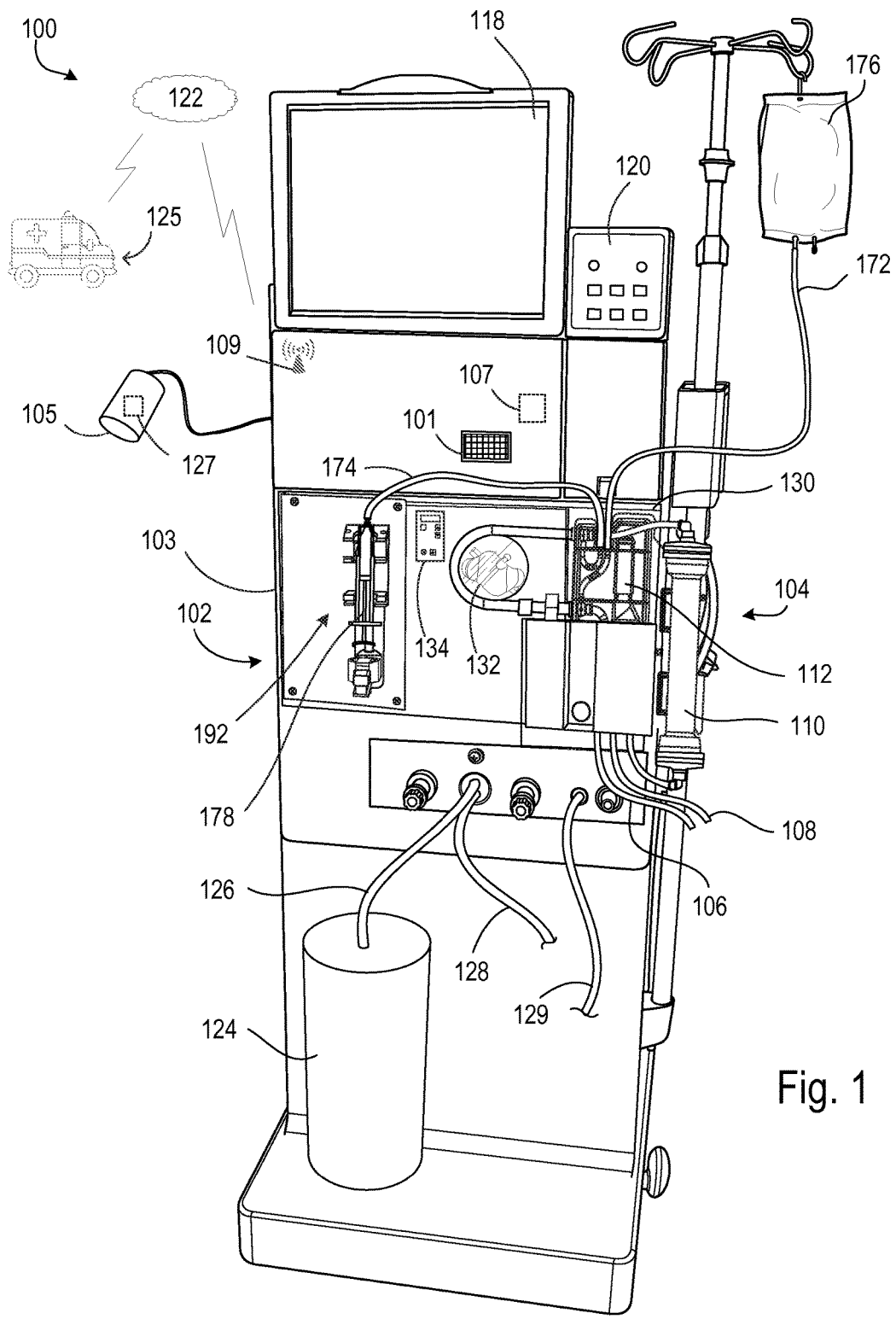
FIG. 1 is a front perspective view of a hemodialysis machine that is connected to a network.

FIG. 1 shows a hemodialysis system 100 configured to send notifications to remote entities. The hemodialysis system 100 includes a hemodialysis machine 102 to which a disposable blood component set 104 that forms a blood circuit is connected. During hemodialysis, arterial and venous patient lines 106, 108 of the blood component set 104 are connected to a patient and blood is circulated through various blood lines and components, including a dialyzer 110, of the blood component set 104. At the same time, dialysate is circulated through a dialysate circuit formed by the dialyzer 110 and various other dialysate components and dialysate lines connected to the hemodialysis machine 102. Many of these dialysate components and dialysate lines are located inside the housing 103 of the hemodialysis machine 102, and are thus not visible in FIG. 1. The dialysate passes through the dialyzer 110 along with the blood. The blood and dialysate passing through the dialyzer 110 are separated from one another by a semi-permeable structure (e.g., a semi-permeable membrane and/or semi-permeable microtubes) of the dialyzer 110. As a result of this arrangement, toxins are removed from the patient's blood and collected in the dialysate. The filtered blood exiting the dialyzer 110 is returned to the patient. The dialysate that exits the dialyzer 110 includes toxins removed from the blood and is commonly referred to as "spent dialysate." The spent dialysate is routed from the dialyzer 110 to a drain.

One of the components of the blood component set 104 is an air release device 112. The air release device 112 includes a self-sealing vent assembly that allows air to pass through while inhibiting (e.g., preventing) liquid from passing through. As a result, if blood passing through the blood circuit during treatment contains air, the air will be vented to atmosphere as the blood passes through the air release device 112.

As shown in FIG. 1, a dialysate container 124 is connected to the hemodialysis machine 102 via a dialysate supply line 126. A drain line 128 and an ultrafiltration line 129 also extend from the hemodialysis machine 102. The dialysate supply line 126, the drain line 128, and the ultrafiltration line 129 are fluidly connected to the various dialysate components and dialysate lines inside the housing 103 of the hemodialysis machine 102 that form part of the dialysate circuit. During hemodialysis, the dialysate supply line 126 carries fresh dialysate from the dialysate container 124 to the portion of the dialysate circuit located inside the hemodialysis machine 102. As noted above, the fresh dialysate is circulated through various dialysate lines and dialysate components, including the dialyzer 110, that form the dialysate circuit. As the dialysate passes through the dialyzer 110, it collects toxins from the patient's blood. The resulting spent dialysate is carried from the dialysate circuit to a drain via the drain line 128. When ultrafiltration is performed during treatment, a combination of the spent dialysate and excess fluid drawn from the patient is carried to the drain via the ultrafiltration line 129.

The blood component set 104 is secured to a module 130 attached to the front of the hemodialysis machine 102. The module 130 includes a blood pump 132 capable of driving blood through the blood circuit. The module 130 also includes various other instruments capable of monitoring the blood flowing through the blood circuit. The module 130 includes a door that when closed, as shown in FIG. 1, cooperates with the front face of the module 130 to form a compartment sized and shaped to receive the blood component set 104. In the closed position, the door presses certain blood components of the blood component set 104 against corresponding instruments exposed on the front face of the module 130. As described in greater detail below, this arrangement facilitates control of the flow of blood through the blood circuit and monitoring of the blood flowing through the blood circuit.

The blood pump 132 can be controlled by a blood pump module 134. The blood pump module 134 includes a display window, a start/stop key, an up key, a down key, a level adjust key, and an arterial pressure port. The display window displays the blood flow rate setting during blood pump operation. The start/stop key starts and stops the blood pump 132. The up and down keys increase and decrease the speed of the blood pump 132. The level adjust key raises a level of fluid in an arterial drip chamber.

A drug pump 192 also extends from the front of the hemodialysis machine 102. The drug pump 192 is a syringe pump that includes a clamping mechanism configured to retain a syringe 178 of the blood component set 104. The drug pump 192 also includes a stepper motor configured to move the plunger of the syringe 178 along the axis of the syringe 178. A shaft of the stepper motor is secured to the plunger in a manner such that when the stepper motor is operated in a first direction, the shaft forces the plunger into the syringe, and when operated in a second direction, the shaft pulls the plunger out of the syringe 178. The drug pump 192 can thus be used to inject a liquid drug (e.g., heparin) from the syringe 178 into the blood circuit via a drug delivery line 174 during use, or to draw liquid from the blood circuit into the syringe 178 via the drug delivery line 174 during use.

The hemodialysis machine 102 includes a speaker 101, one or more accessories for detecting health conditions of the patient such as a blood pressure cuff 105, a touch screen 118, and a control panel 120. The touch screen 118 and the control panel 120 allow an operator to input various different treatment parameters to the hemodialysis machine 102 and to otherwise control the hemodialysis machine 102. In addition, the touch screen 118 serves as a display. In the example shown in FIG. 1, the speaker 101 is positioned below the touch screen 118 and, together or independently, function to provide information (e.g., alerts) to the patient and the operator of the hemodialysis system 100. Thus, the hemodialysis machine 102 is capable of providing both visual alerts via the touch screen 118 and audio alerts via the speaker 101.

The hemodialysis machine 102 includes a processing module 107 that resides inside the machine and which is configured to communicate with the touch screen 118, the control panel 120, the speaker 101, and the blood pressure cuff 105. The processing module 107 is configured to receive data from the touch screen 118, the control panel 120, and the blood pressure cuff 105 and control the hemodialysis machine 102 based on the received data. For example, the processing module 107 can adjust the operating parameters of the hemodialysis machine 102.

The hemodialysis machine 102 is configured to connect to a network 122. The hemodialysis machine 102 includes a transceiver 109 that is configured to facilitate the connection to the network 122. Other medical devices (e.g., other dialysis machines) may be configured to connect to the network 122 and communicate with the hemodialysis machine 102. Similarly, one or more remote entities 125, such as 911 EMS or other emergency personnel, may be able to connect to the network 122 and communicate with the hemodialysis machine 102. In this way, the transceiver 109 of the hemodialysis machine 102 can send a notification to the remote entity 125 through the network 122.

The hemodialysis machine 102 can also include a motion sensor 127 for detecting motion of the patient. In the example shown in FIG. 1, the motion sensor 127 is incorporated into the blood pressure cuff 105. In some implementations, the motion sensor 127 includes one or both of an accelerometer and a gyroscope. The blood pressure cuff 105 also includes one or more other sensors for detecting a health condition (e.g., the blood pressure) of the patient. The processing module 107 receives information related to the motion of the patient and information related to the health condition of the patient from the blood pressure cuff 105. Based at least in part on this received information, the processing module 107 identifies an emergency condition experienced by the patient. In response to identifying the emergency condition, the processing module 107 can instruct the transceiver 109 to send a notification that includes patient information to the remote entity 125 (e.g., using the network 122).

Figure 2:
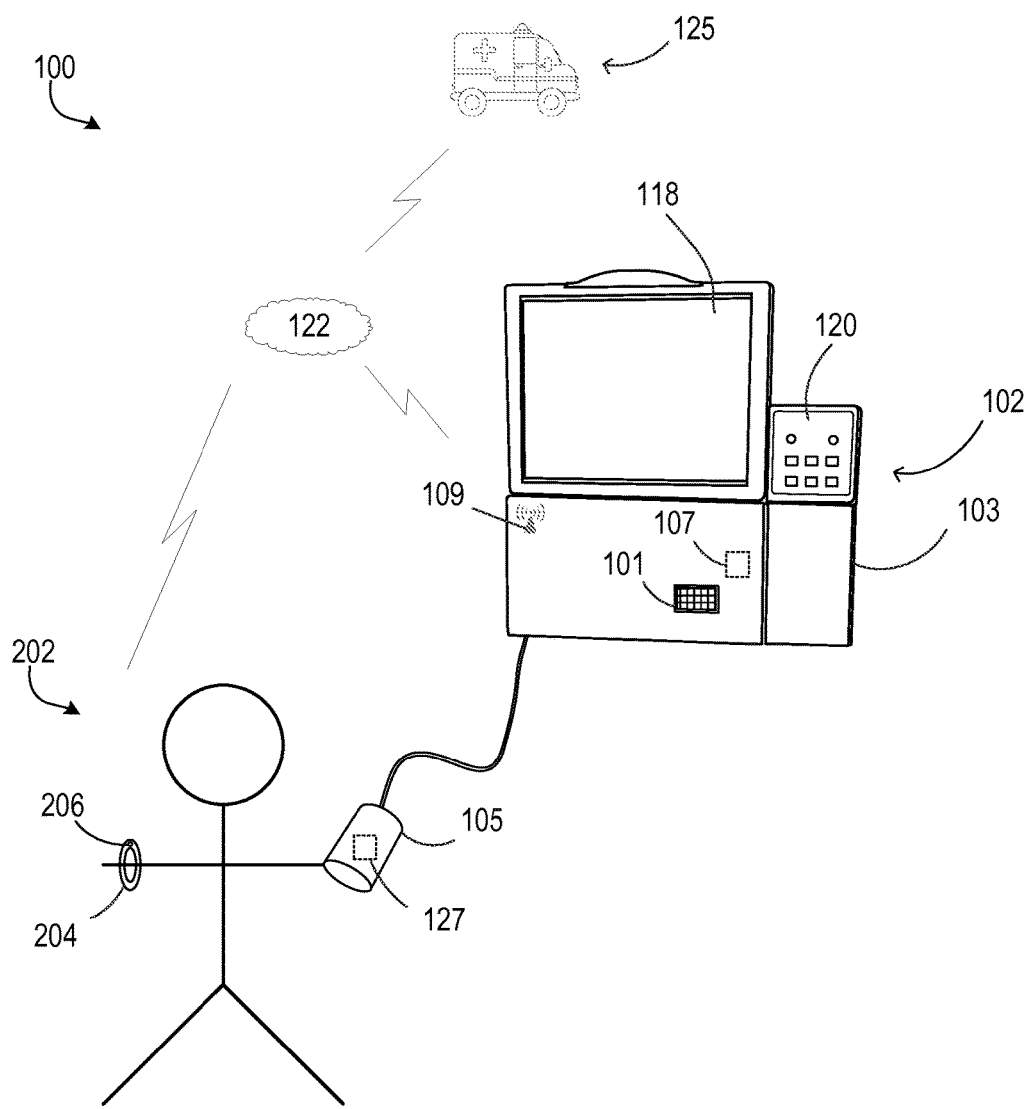
FIG. 2 shows an example of a patient who is receiving treatment from the hemodialysis machine and who is wearing an alert mechanism.

FIG. 2 shows an example of a patient 202 who is receiving treatment from the hemodialysis machine 102. The hemodialysis machine 102 can determine whether the current conditions of the patient 202 are such that emergency personnel should be notified.

The patient 202 is wearing the blood pressure cuff 105. The motion sensor 127 disposed in the blood pressure cuff 105 measures information related to motion of the patient 202. One or more other sensors in the blood pressure cuff 105 measure information related to the blood pressure of the patient 202. The processing module 107, which is controlling functions of the patient's 202 treatment, receives information related to a status of the dialysis treatment, the information related to the motion of the patient 202, and the information related to the blood pressure of the patient 202.

Using this information, the processing module 107 identifies an emergency condition based at least in part on the received information. For example, the processing device 107 may determine that the patient 202 has not moved for a predetermined amount of time (e.g., 1 hour) based on the information related to the motion of the patient 202. The processing device 107 may further determine that the patient's 202 blood pressure is above or below a predetermined threshold based on the information related to the blood pressure of the patient 202. In response to these determinations, the processing device identifies an emergency condition.

In some implementations, the identification of an emergency condition by the processing module 107 is based in part on a status of the dialysis treatment of the patient 202. In some examples, if the dialysis treatment is in a stage that is generally considered to be dangerous or high-risk, the processing module 107 may use different thresholds for identifying an emergency condition under the particular circumstances. For example, as the arterial and venous patient lines 106, 108 (shown in FIG. 1) are being connected to the patient 202—which may be considered a relatively dangerous stage of the dialysis treatment—the processing module 107 may identify an emergency condition if the patient's 202 blood pressure is above 140/90 mmHg. On the other hand, during later stages of the dialysis treatment (e.g., after the patient 202 has been receiving dialysis treatment for a predefined period of time and is determined to be in a steady state), the processing module 107 may identify an emergency condition if the patient's 202 blood pressure is above 160/100 mmHg.

In some implementations, the processing device 107 may also receive information related to a sleep state of the patient 202. Based on the information related to the sleep state of the patient 202, the processing device 107 may attribute the patient's 202 lack of motion to the patient 202 being asleep, and thus refrain from identifying an emergency condition, e.g., due to a lack of movement, unless other criteria are satisfied.

When an emergency condition is identified, the processing module 107 instructs the transceiver 109 to send a notification to one or more remote entities 125. For example, the remote entity 125 may be an Emergency Medical Services (EMS) entity, such as 911 EMS, and the transceiver 109 may send a notification to 911 EMS. The 911 EMS may be connected to the network 122 to which the hemodialysis machine 102 is connected, and the notification can be sent to the 911 EMS over the network 122. The notification can include patient information such as the patient's name, address, location, medical condition, demographic information, preferred hospital, medication list, allergies, treatment information, emergency contact, and associated medical personnel. The notification can be sent through one or more mediums, such as through email, text, phone call, or some other communication channel.

Upon receiving the notification, the 911 EMS is provided with the information needed to find the patient 202 and provide emergency treatment. For example, the notification may include the geographic location of the hemodialysis machine 102 (e.g., GPS coordinates), a medical condition that lead to the emergency condition being identified, and information related to the dialysis treatment that was being administered when the emergency condition was identified. When provided this information, the 911 EMS is better equipped to dispatch appropriate resources under the patient's 202 particular circumstances. For example, if the emergency condition was identified based at least in part on the patient's 202 blood pressure exceeding or falling below a safe threshold, the 911 EMS may decide to dispatch medical personnel who specialize in blood pressure problems to better assist the patient 202 as compared to general emergency response personnel.

In some situations, the processing device 107 may not have received enough information to identify that an emergency condition exists above a threshold of certainty (e.g., 90% certainty). To reduce the occurrence of an emergency condition being falsely identified by the processing device 107, the hemodialysis system 100 may generate an intermediate alert indicating that a potential emergency condition has been identified. Prior to sending a notification to the 911 EMS, the hemodialysis system 100 can be instructed to refrain from sending the notification if the potential emergency condition is not, in fact, an emergency condition.

As an example, the hemodialysis system 100 includes an alert mechanism 204. The alert mechanism 204 may be worn by the patient 202 and can be configured to generate an alert directed at the patient 202 indicating that a potential emergency condition has been identified. The alert mechanism 204 may be in the form of a bracelet, as shown in FIG. 2. The alert mechanism 204 is configured to communicate with the hemodialysis machine 102 (e.g., directly or through the network 122).

In an example, if the processing device 107 determines that the patient 202 has not moved for a predetermined amount of time (e.g., 1 hour), the alert mechanism 204 may generate an alert directed at the patient. The alert mechanism 204 can include one or more modules for generating audible, visual, or haptic alerts, to name a few. For example, upon determining that the patient 202 has not moved for the predetermined amount of time, the alert mechanism 204 may vibrate, indicating to the patient 202 that a potential emergency condition has been identified.

The alert mechanism 204 can also be configured to receive, from the patient 202, input indicating that the potential emergency condition is not an emergency condition (e.g., the potential emergency condition is a false positive). The alert mechanism 204 can include an input mechanism, such as a button 206, that the patient 202 can invoke (e.g., tap or press) to indicate that the potential emergency condition is not an emergency condition. In this example, the patient 202 may not be experiencing an emergency condition. That is, the patient 202 may have not moved for the predetermined amount of time because the patient 202 was resting or sleeping, as opposed to having lost consciousness from blood loss or another severe medical incident. To indicate that the patient 202 is not experiencing an emergency condition, the patient 202 can press the button 206 on the alert mechanism 204, thereby preventing the 911 EMS from receiving a notification that an emergency condition exists.

In some situations, the potential emergency condition is, in fact, an emergency condition. To indicate that the patient 202 is experiencing an emergency condition, the patient 202 may refrain from pressing the button 206 on the alert mechanism 204 that would otherwise prevent the 911 EMS from receiving a notification. For example, if the patient is in a dangerous medical state and has lost consciousness, the patient may not be awoken by an audible alert. In some examples, the hemodialysis system 100 is configured to cause the notification to be sent to the 911 EMS if input is not received by the patient 202 within a predetermined amount of time. As such, failure to respond to the alert may indicate that the patient 202 is experiencing an emergency. In some examples, the alert mechanism 204 includes an input mechanism that the patient 202 can execute to indicate that the potential emergency condition is an emergency condition, thereby causing the notification to be sent to the 911 EMS immediately. In some implementations, this could be a second input mechanism in addition to the input mechanism to indicate that the potential emergency condition is not an emergency condition. In some implementations, this could be an input mechanism used instead of the input mechanism to indicate that the potential emergency condition is not an emergency condition In some implementations, the alert mechanism 204 includes a storage device. The alert mechanism 204 may be configured to receive and store patient information from the hemodialysis machine 102. As described above, the alert mechanism 204 may be in wireless communication with the hemodialysis machine 102 (e.g., through the network 122) and be configured to wireless receive the patient information from the hemodialysis machine 102. In some example, in response to receiving a notification indicating that an emergency condition exists, the 911 EMS travels to the patient 202 to administer medical treatment. In some cases, the patient 202 may need to be transported to a medical facility to receive treatment. By having patient information stored on the alert mechanism 204, and because the alert mechanism 204 can be worn by the patient 202, information that may be helpful for administering treatment to the patient 202 accompanies the patient 202 wherever he or she may be transported. This will occur even if the 911 EMS personnel (or equivalent) are not initially aware that the stored patient information is available to them.

Figure 3:
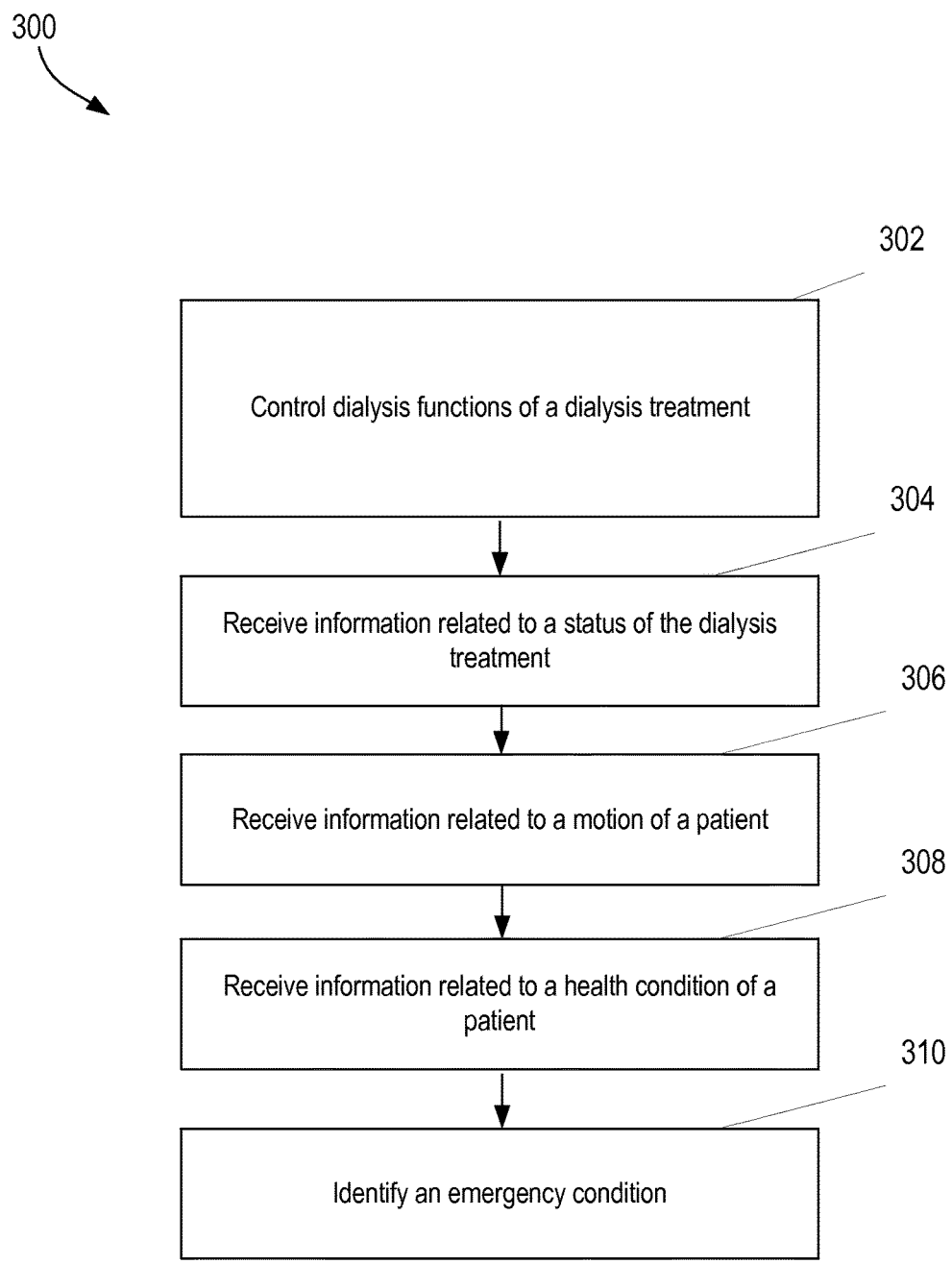
FIG. 3 shows a flowchart illustrating steps that can be performed by a processing module of the hemodialysis machine.

FIG. 3 shows a flowchart illustrating steps that can be performed by a processing module (e.g., the processing module 107 of FIGS. 1 and 2). The processing module controls functions related to a dialysis treatment of a patient (302). The processing module may determine and control parameters of the dialysis treatment such that the treatment is tailored to the patient. For example, the parameters can control aspects of the treatment such as the length of the treatment session, the drug types and quantities administered during the treatment session, and the blood flow rate settings of the blood pump, to name a few. During treatment, the processing module receives information related to a status of the dialysis treatment (304). For example, the processing module may receive feedback from the hemodialysis machine that indicates the progress of the treatment or the patient's response to the treatment. The processing module also receives information related to the motion of the patient from a first sensor (306). For example, the processing module may receive information from a motion sensor that may be included in an accessory of the hemodialysis machine. The information may indicate an amount of time during which the patient has not moved. The processing module also receives information related to a health condition of the patient from a second sensor (308). One example of a health condition of the patient is blood pressure. For example, an accessory (e.g., the same accessory that includes the motion sensor) may be a blood pressure cuff that includes a sensor for detecting the patient's blood pressure. The processing module can identify an emergency condition based at least in part on the received information (310). For example, the processing module may first analyze the information related to the status of the dialysis treatment to determine conditions that, if satisfied, indicate that an emergency condition exists. The processing module may then analyze the information related to the motion of the patient and the information related to the health condition of the patient to determine whether the conditions are satisfied.

In an example, the information related to the status of the dialysis treatment indicates that the patient is near the end of a particular dialysis treatment session. A risk associated with a particular dialysis treatment is typically greater near the beginning of the treatment and diminishes as the treatment progresses. Based on this information, the processing module determines that an emergency condition exists if the patient's blood pressure is above 160/100 mmHg and the patient has not moved for 1 hour. Had the patient been in the early stages of the particular dialysis treatment session (and thus at higher risk), the processing module may have determined that an emergency condition exists if the patient's blood pressure is above 140/90 mmHg and the patient has not moved for 30 minutes.

The processing module analyzes the information related to the motion of the patient and determines that the patient has not moved for 65 minutes. The processing module also analyzes the information related to the health condition of the patient and determines that the patient's blood pressure is 165/105 mmHg. In response, the processing module causes a notification to be sent to one or more remote entities, such as 911 EMS. The notification includes patient information that may be helpful for administering treatment to the patient. The patient information can include a geographic location of the patient to aid the 911 EMS in finding the patient.

Figure 4:
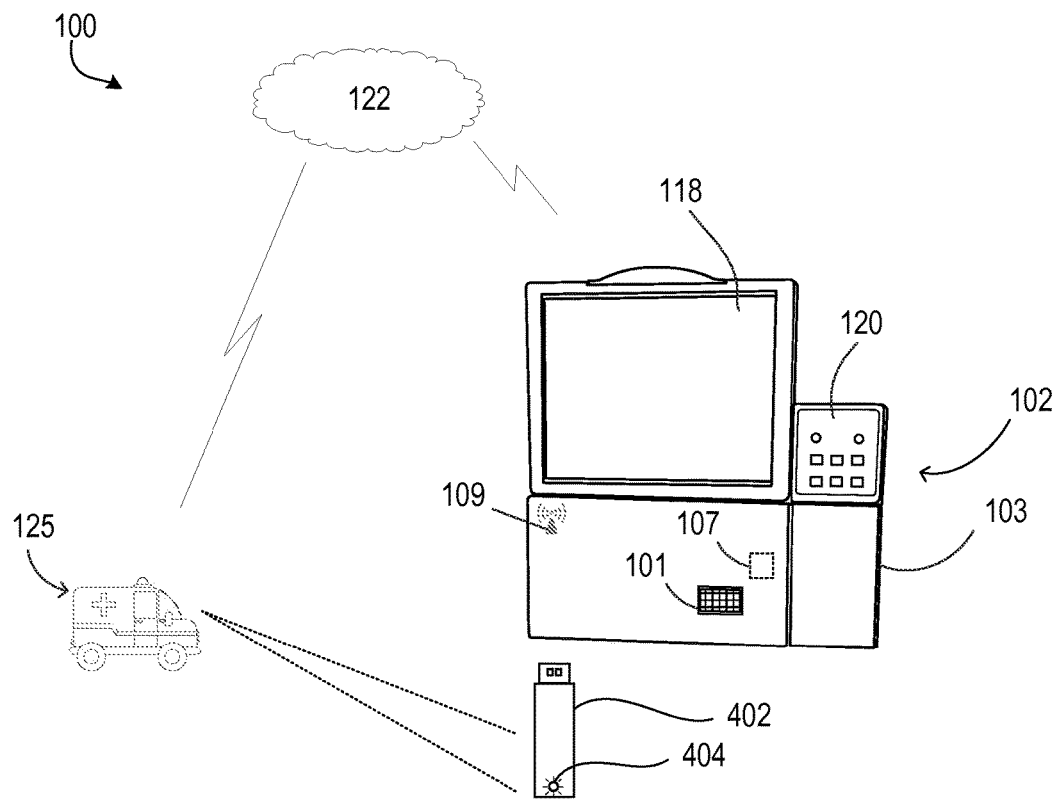
FIG. 4 shows an example of a USB memory device that is configured to communicate with the hemodialysis machine.

FIG. 4 shows an example of a data communications interface that includes a portable memory device, such as a universal serial bus (USB) memory device 402 that is configured to communicate with the hemodialysis machine 102. The USB memory device 402 mates with a port, such as a USB port, on the hemodialysis machine 102.

An interface control system, such as a USB interface control system, of the hemodialysis machine 102 manages the communication between the USB memory device 402 and the hemodialysis machine 102. For example, the patient 202 or the operator of the hemodialysis machine 102 can manage the download of patient information to the USB memory device 402 using the USB interface control system. As with the implementation of the alert mechanism 204 of FIG. 2 described above, the USB memory device 402 can accompany the patient 202 if the patient 202 is transported to a medical facility. As such, information that may be helpful for administering treatment to the patient 202 accompanies the patient 202.

The USB memory device 402 includes an alert mechanism 404 that is configured to generate an alert directed at an emergency responder. The alert informs the emergency responder that the USB memory device 402 contains patient information that is relevant to the patient's 202 emergency condition. In this way, the alert mechanism 404 notifies the emergency responder that the USB memory device 402 should be taken from the hemodialysis machine 102 and should accompany the patient 202 (e.g., to the medical facility). In the example shown in FIG. 4, the alert mechanism 404 is a light that generates an alert in the form of a flashing light that is intended to catch the emergency responder's attention.

While the portable memory device is principally described in FIG. 4 as the USB memory device 402, in some implementations, the portable memory device may be implemented using other appropriate data transmission protocols and components. For example, in some implementations, the portable memory device may be incorporated in connection with a smartphone, a tablet, and/or anther portable computing device and may include wireless transmission components for exchanging wireless signals and data transmissions between the portable memory device and the hemodialysis machine 102. In some implementations, the signals and data exchanged between the portable memory device and the hemodialysis machine 102 may be encrypted according to appropriate security standards and protocols.

A method of using the hemodialysis system 100 to administer a dialysis treatment to a patient will now be described.

Figure 5:
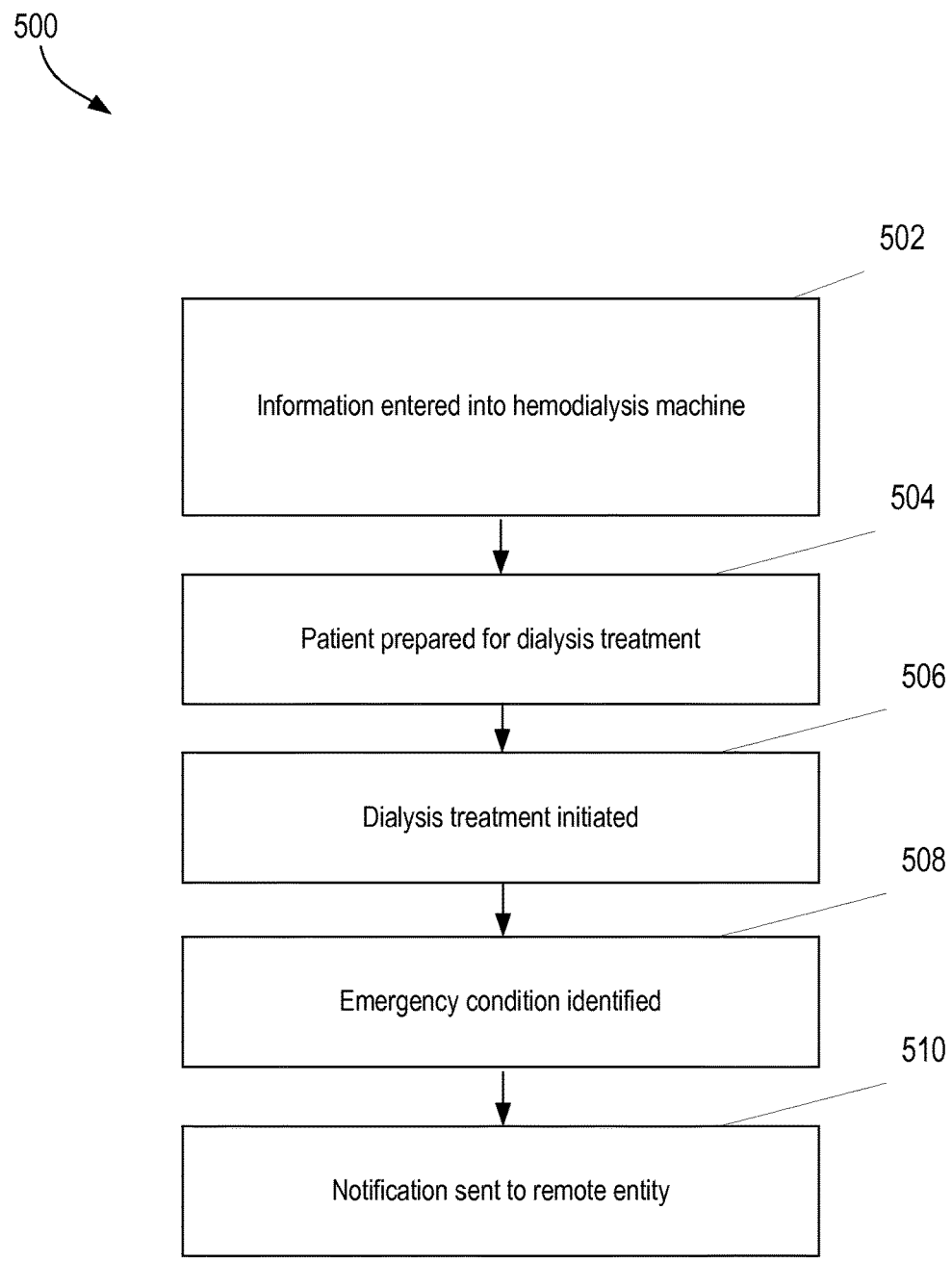
FIG. 5 shows a flowchart illustrating a method of administering a dialysis treatment to a patient.

FIG. 5 shows a flowchart illustrating a method of administering a dialysis treatment to a patient. Before treatment begins, an operator enters information into the hemodialysis machine 102 via the touch screen 118 and/or the control panel 120 (502). The operator typically enters patient information and medical treatment information, and the hemodialysis machine 102 determines appropriate operating parameters for the patient's treatment. Once the patient information and the medical treatment information are entered, the operator prepares the patient for dialysis treatment (504). Referring back to FIG. 1, the arterial and venous patient lines 106, 108 are connected to the patient. The hemodialysis treatment is then initiated (506). The blood pressure cuff 105 is applied to the patient's arm. During hemodialysis, blood is circulated through the blood circuit (i.e., the various blood lines and blood components, including the dialyzer 110, of the blood component set 104). At the same time, dialysate is circulated through the dialysate circuit (i.e., the various dialysate lines and dialysate components, including the dialyzer 110).

During treatment, one or more emergency conditions may arise (508). For example, the processing module 107 of the hemodialysis machine 102 may determine that the patient has not moved for a predetermined period of time and that the patient's blood pressure is dangerously high. Based at least in part on this information, the processing module 107 may identify an emergency condition experienced by the patient.

When the emergency condition is identified, the processing module 107 can instruct the transceiver 109 to send a notification that includes patient information to the remote entity 125 (510). The patient information can include information that was input into the hemodialysis machine 102 before treatment commenced.

The remote entity 125 may be 911 EMS. The notification can include information related to the location of the patient 202 that the 911 EMS can use to find the patient 202. The notification can also include information related to the medical condition of the patient 202 and the dialysis treatment that the patient 202 was receiving when the emergency condition arose. Based on the information contained in the notification, the 911 EMS can administer appropriate medical care to the patient.

In another example, before the notification is sent to the 911 EMS, the hemodialysis system 100 generates an intermediate alert indicating that a potential emergency condition has been identified. The intermediate alert is generated by an alert mechanism 204 worn by the patient 202. The hemodialysis machine 102 is configured to receive input from the patient 202, through the alert mechanism 204, which indicates whether the potential emergency condition is, in fact, an emergency condition. If the patient 202 indicates that the potential emergency condition is an emergency condition, the notification is sent to the 911 EMS. If the patient 202 indicates that the potential emergency condition is not an emergency condition, the notification is not sent. If the patient 202 fails to respond to the intermediate alert within a predetermined amount of time, the notification is sent to the 911 EMS.

When the 911 EMS arrives to assist the patient 202, it may be determined that the patient 202 needs to be transported to a medical facility to receive appropriate medical care. Patient information and other information related to the emergency condition is stored on the alert mechanism 204. Because the alert mechanism 204 is worn by the patient 202, the information is kept with the patient 202 and can be accessed by medical personnel at the medical facility.

In another example, patient information and other information related to the emergency condition is stored on a USB memory device 402 that communicates with the hemodialysis machine 102. As the patient 202 receives hemodialysis treatment, information related to the treatment is stored on the USB memory device 402. The USB memory device 402 also includes an alert mechanism 404. The alert mechanism 404 is configured to generate an alert when an emergency condition is identified. The alert mechanism 404 is a light, and the alert is in the form of a flashing light. When the 911 EMS arrives at the patient 202, a member of the 911

EMS sees the flashing light and is reminded to take the USB memory device 402 along with the patient 202.

While certain implementations have been described, other implementations are possible.

While the accessory has been described as being a blood pressure cuff 105, in some implementations, the dialysis machine 102 can include one or more accessories instead of or in addition to the blood pressure cuff 105.

In some implementations, the accessory is a device that includes a heart rate sensor. If the patient's heart rate is above or below a predetermined threshold, the processing device may identify an emergency condition.

In some implementations, the accessory is a device that includes a moisture sensor. The moisture sensor may be positioned near the insertion site of a needle into the patient (e.g., a needle that is delivering or extracting medical fluid from the patient). If the moisture sensor detects moisture, this may indicate that the needle has been dislodged from the patient and the medical fluid has made contact with the moisture sensor. In response, the processing device may identify an emergency condition.

While the dialysis machine has been described as communicating with remote entities through the network, in some implementations, the hemodialysis machine is configured to communicate directly with remote entities. For example, the transceiver may be configured to facilitate a direct connection between the hemodialysis machine and a remote entity.

While the motion sensor has been described as being incorporated into the blood pressure cuff, in some implementations, the motion sensor is instead incorporated into some other part of the hemodialysis system. In some implementations, the motion sensor is incorporated into another accessory of the dialysis machine. In some implementations, the motion sensor is an optical sensor that is configured to detect motion.

While the alert indicating that a potential emergency condition has been identified has been described as being generated by the alert mechanism, the alert indicating that a potential emergency condition has been identified can be communicated to the patient in other ways. For example, the touch screen or the speaker of the hemodialysis machine may generate the alert. Similarly, while the input received from the patient indicating that the potential emergency condition is not an emergency condition has been described as being received by the alert mechanism, the input can be received by the patient in other ways. For example, the patient may indicate that the potential emergency condition is not an emergency condition using the touch screen, the control panel, or an accessory of the dialysis machine.

While the input mechanism of the alert mechanism has been described as being a button, the input mechanism can take on other forms. In some implementations, the input mechanism is a touch screen on the alert mechanism. In some implementations, the input mechanism is configured to receive audible input (e.g., voice commands).

While the alert mechanism has been described as including a second input mechanism that the patient can execute to indicate that the potential emergency condition is an emergency condition, the indication can be made by the patient in other ways. For example, the patient may indicate that the potential emergency condition is an emergency condition using the touch screen, the control panel, or an accessory of the dialysis machine.

While the alert mechanism has been described as including a second input mechanism that the patient can execute to indicate that the potential emergency condition is an emergency condition, in some implementations, the patient can cause a notification to be sent to the one or more remote entities without the processing device first identifying that a potential emergency condition exists. That is, the patient can cause the notification to be sent to the remote entity without any other conditions being satisfied. In some implementations, the patient can cause the notification to be sent to the remote entity by executing an input mechanism on the alert mechanism. In some implementations, the patient can cause the notification to be immediately sent to the remote entity using the touch screen, the control panel, or an accessory of the dialysis machine.

While the alert mechanism of the portable memory device has been described as being a light, the alert mechanism can take on other forms. In some implementations, the alert mechanism is a speaker that generates an audio tone that is intended to catch the emergency responder's attention. In some implementation, the audio tone is a spoken voice that instructs the emergency responder to remove the portable memory device from the dialysis machine and to have the portable memory device accompany the patient.

While the remote entity has been described as being 911 EMS, the remote entity can be one or more other persons. In some implementations, the remote entity is a doctor, a nurse, or an emergency contact of the patient. In some implementations, the remote entity is an emergency service offered by a particular country (e.g., such as "112" emergency services in many European countries). In some implementations, the transceiver sends a notification to more than one remote entity when the processing module identifies an emergency condition.

While the portable memory device has been described as automatically storing information related to the dialysis treatment, in some implementations, the information is stored in response to user input. In some implementations, the dialysis machine includes a button that, when engaged, causes patient information to be downloaded to the portable memory device and a notification to be sent to one or more remote entities. In some implementations, the button is a physical button positioned on the housing of the dialysis machine. In some implementations, the button is a virtual button on the touch screen of the dialysis machine. The notification can include some or all of the patient information. In some implementations, such a button is included on the portable memory device itself.

While the notification has been described as being sent by a hemodialysis machine, the notification could alternatively be sent by other types of medical treatment systems. Examples of other medical treatment systems that may employ the techniques described herein include hemofiltration systems, hemodiafiltration systems, apheresis systems, cardiopulmonary bypass systems, and peritoneal dialysis systems.

Peritoneal dialysis (PD) utilizes the patient's own peritoneum, a membranous lining of the abdominal body cavity. With its good perfusion properties, the peritoneum is capable of acting as a natural semi-permeable membrane for transferring water and waste products to a type of dialysate solution known as PD solution introduced temporarily into the patient's abdominal cavity. An access port is implanted in the patient's abdomen and the PD solution is infused usually by a pump into the patient's abdomen through a patient line and left to dwell for a period of time and then drained out. This procedure is usually repeated several times for a complete treatment. A PD treatment typically lasts for several hours, and often begins with an initial drain cycle to empty the peritoneal cavity of spent dialysate. The sequence then proceeds through a succession of fill, dwell, and drain phases that follow one after the other.

The PD solution itself is usually sourced from a set of pre-filled bags which are connected via tubing to the machine for warming and pumping PD solution through the patient line. The machine itself includes a console with a computer and pumps and valves controlled by the computer to pull PD solution from the correct bag and pump it to the patient, and then, after a programmed interval, draw fluid out of the patient to a drain or drain bag. The fluid lines may include a removable flexible plastic cassette with pump chambers, valve elements, and channels connected to the patient and drain lines and PD solution bags via tubing. The cassette may be inserted into a pressurized door where it mates with the pumping mechanism and valve actuators.

Implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible program carrier, for example a computer-readable medium, for execution by, or to control the operation of, a processing system. The computer readable medium can be a machine readable storage device, a machine readable storage substrate, a memory device, a composition of matter effecting a machine readable propagated signal, or a combination of one or more of them.

The term "computer system" may encompass all apparatus, devices, and machines for processing data, including by way of example a programmable processor (e.g., processing module), a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of nonvolatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. The components of the system can be interconnected by any form or medium of digital data communication, e.g., a communication network. Examples of communication networks include a local area network ("LAN") and a wide area network ("WAN"), e.g., the Internet.

A number of implementations have been described. Nevertheless, it will be understood that various modifications may be made without departing from the spirit and scope of the invention. Accordingly, other implementations are within the scope of the following claims.

What is claimed is:

1. A dialysis system comprising a dialysis machine, the dialysis machine comprising:
    a first sensor for detecting motion of a patient;
    a second sensor for detecting a health condition of the patient;
    a processing module for:
        controlling dialysis functions of a dialysis treatment;
        receiving information related to a status of the dialysis treatment in which toxins are removed from blood of the patient;
        receiving, from the first sensor, information related to the motion of the patient;
        determining, based on the information related to the motion of the patient, that the patient has not moved for a predetermined amount of time;
        receiving, from the second sensor, information related to the health condition of the patient;
        identifying a potential emergency condition based at least in part on the determination that the patient has not moved for the predetermined amount of time; and
        identifying an emergency condition based at least in part on the determination that the patient has not moved for the predetermined amount of time, the information related to the health condition of the patient, and the information related to the status of the dialysis treatment;
    a first alert mechanism for:
        generating an alert directed at the patient indicating that the potential emergency condition has been identified; and
        receiving, from the patient, an input indicating that the potential emergency condition is not an emergency condition, wherein the identifying the emergency condition includes identifying the potential emergency condition as an emergency condition because an input was not received;
    a universal serial bus (USB) data communications interface comprising:
        a USB port on the dialysis machine that interfaces with a portable USB memory device that includes a second alert mechanism configured to generate an alert directed at an emergency responder, the alert for informing the emergency responder that the portable USB memory device contains patient information that is relevant to an emergency condition of the patient, and
        a USB interface control system for managing download of the patient information to the portable USB memory device in response to the identification of the emergency condition; and a transceiver for:
   in response to identifying the emergency condition, sending a notification that includes patient information to one or more remote entities.

2. The dialysis system of claim 1, wherein the dialysis machine comprises:
   a dialysate cassette configured to be fluidly connected to one or more dialysate containers by one or more dialysate container lines; and
   a dialysate pump for:
      pumping dialysate from one or more of the dialysate containers, through the dialysate cassette, through a patient line, to an abdomen of the patient; and
      drawing spent dialysate from the abdomen of the patient, through a drain line, through the dialysate cassette, to a drain, wherein the spent dialysate includes toxins that are removed from the blood of the patient.

3. The dialysis system of claim 1, wherein the dialysis machine comprises:
   a dialysate pump for pumping dialysate through a first portion of a dialyzer; and
   a blood pump for drawing blood from the patient through a second portion of the dialyzer, wherein the dialyzer is configured to remove toxins from the blood of the patient and collect the toxins in the dialysate.

4. The dialysis system of claim 1, wherein the second sensor is a blood pressure sensor and the information related to the health condition of the patient is blood pressure information.

5. The dialysis system of claim 1, wherein the second sensor is a heart rate sensor and the information related to the health condition of the patient is heart rate information.

6. The dialysis system of claim 1, wherein the second sensor is a moisture sensor.

7. The dialysis system of claim 6, wherein the moisture sensor is for detecting whether a needle has been dislodged from the patient.

8. The dialysis system of claim 1, comprising a device that is in wireless communication with the dialysis machine, the device including the alert mechanism and a button that, when engaged by the patient, indicates that the potential emergency condition is not an emergency condition.

9. The dialysis system of claim 8, wherein the device is configured to wirelessly receive patient information from the dialysis machine.

10. The dialysis system of claim 8, wherein the dialysis machine includes a button that, when engaged, causes the notification that includes the patient information to be sent to the one or more remote entities.

11. The dialysis system of claim 8, wherein the device is a bracelet.

12. The dialysis system of claim 1, wherein the patient information includes location information related to the patient.

13. The dialysis system of claim 12, wherein the location information related to the patient includes a geographic location of the dialysis machine.

14. The dialysis system of claim 1, wherein the patient information includes one or more of a medical condition of the patient, demographic information of the patient, a preferred hospital of the patient, a medication list of the patient, allergies of the patient, information related to the patient's treatment, emergency contact associated with the patient, and medical personnel associated with the patient.

15. The dialysis system of claim 1, wherein the remote entities include one or more of 911 EMS, a nurse, a doctor, and an emergency contact of the patient.

16. The dialysis system of claim 1, wherein the alert mechanism electronics are located directly on the portable memory device.

17. The dialysis system of claim 1, wherein the alert is indicative of the patient having not moved for the predetermined amount of time.

18. The dialysis system of claim 1, wherein the input is indicative of the patient being conscious.

19. A dialysis machine comprising:
   a processing module for:
      controlling dialysis functions of a dialysis treatment;
      receiving information related to a status of the dialysis treatment in which toxins are removed from blood of a patient;
      receiving information related to motion of the patient;
      determining, based on the information related to the motion of the patient, that the patient has not moved for a predetermined amount of time; and
      receiving information related to a health condition of the patient; and
   a universal serial bus (USB) data communications interface comprising:
      a USB port on the dialysis machine that interfaces with a portable USB memory device that includes an alert mechanism configured to generate an alert directed at an emergency responder, the alert for informing the emergency responder that the portable USB memory device contains patient information that is relevant to an emergency condition of the patient; and
      a USB interface control system for managing download of the patient information to the portable USB memory device, the patient information based at least in part on the determination that the patient has not moved for the predetermined amount of time, the information related to the health condition of the patient, and the information related to the status of the dialysis treatment.

20. The dialysis machine of claim 19, further comprising:
   a dialysate cassette configured to be fluidly connected to one or more dialysate containers by one or more dialysate container lines; and
   a dialysate pump for;
      pumping dialysate from one or more of the dialysate containers, through the dialysate cassette, through a patient line, to an abdomen of the patient; and
      drawing spent dialysate from the abdomen of the patient, through a drain line, through the dialysate cassette, to a drain, wherein the spent dialysate includes toxins that are removed from the blood of the patient.

21. The dialysis machine of claim 19, further comprising:
   a dialysate pump for pumping dialysate through a first portion of a dialyzer; and
   a blood pump for drawing blood from the patient through a second portion of the dialyzer, wherein the dialyzer is configured to remove toxins from the blood of the patient and collect the toxins in the dialysate.

22. The dialysis machine of claim 19, further comprising:
   a button that, when engaged, causes:
      the patient information to be downloaded to the portable USB memory device; and
      a notification to be sent to one or more remote entities that includes some or all of the patient information.

23. The dialysis machine of claim 22, wherein the button is a physical button positioned on a housing of the dialysis machine.

24. The dialysis machine of claim 22, wherein the button is a virtual button on a touch screen of the dialysis machine.

25. The dialysis machine of claim 19, wherein the alert is an audio tone.

26. The dialysis machine of claim 19, wherein the alert is a flashing light.

27. The dialysis machine of claim 19, wherein the patient information includes one or more of a medical condition of the patient, demographic information of the patient, a preferred hospital of the patient, a medication list of the patient, allergies of the patient, information related to the patient's treatment, and medical personnel associated with the patient.

* * * * *